United States Patent [19]
Feinberg et al.

[11] Patent Number: 5,897,505
[45] Date of Patent: Apr. 27, 1999

[54] SELECTIVE TISSUE CONDUCTANCE/ THERMOGRAPHY SENSOR APPARATUS

[76] Inventors: Barry I. Feinberg, 3565 Pennridge Dr., Bridgeton, Mo. 63044; Francis L. Cassady, 2905 Pentecostal Rd., Edwardsville, Ill. 62025

[21] Appl. No.: 08/854,903

[22] Filed: May 13, 1997

[51] Int. Cl.$^6$ .................................................. A61B 5/05
[52] U.S. Cl. ............................................. 600/547; 600/549
[58] Field of Search .................................. 600/547, 549, 600/393, 372

[56] References Cited

U.S. PATENT DOCUMENTS

| | | | |
|---|---|---|---|
| 3,894,532 | 7/1975 | Morey | 128/2.1 |
| 4,129,125 | 12/1978 | Lester et al. | 600/549 |
| 4,697,599 | 10/1987 | Woodley et al. | 128/734 |
| 4,797,840 | 1/1989 | Fraden | 600/549 |
| 4,809,707 | 3/1989 | Kraft et al. | 600/549 |
| 4,917,092 | 4/1990 | Todd et al. | 600/547 |
| 5,017,019 | 5/1991 | Pompei | 600/549 |
| 5,399,018 | 3/1995 | Hollander et al. | 374/121 |
| 5,588,440 | 12/1996 | Cowie | 600/547 |

OTHER PUBLICATIONS

Epi–Scan 500 Operators Manual, The Epi–Scan Corporation.

"10. Selective Tissue Conductance in the Assessment of Sympathetically Mediated Pain," by David R. Longmire and Winston C. V. Parris, pp. 147–160.

"Tutorial 11: Clinical Neurophysiology of Pain–Related Sympathetic Sudomotor Dysfunction", Longmire and Woodley, "Pain Digest," Springer–Verlag New York Inc., 1993, pp. 3:202–209.

*Primary Examiner*—Max Hindenburg
*Assistant Examiner*—Charles Marmor, II
*Attorney, Agent, or Firm*—Frost & Jacobs LLP

[57] ABSTRACT

A diagnostic device for measuring selective tissue conductance and temperature is described which can be used to assess pain, abnormal sensation or sympathetic dysfunction in a human being or animal. Two spaced-apart electrodes are mounted together for measuring conductance of tissue over a selected region. A temperature sensor is positioned adjacent the electrodes for measuring tissue temperature in the selected region. A circuit is provided for indicating measured temperature and conductance to a user for localizing a region of sympathetic nerve dysfunction. In preferred form, the device indicates measured temperature and conductance visually and/or audibly by utilizing a measurement of both selective tissue conductance and temperature together. A more specific and useful diagnosis of sympathetic nerve dysfunction may be made than through the use of sensing either conductance or temperature separately.

12 Claims, 4 Drawing Sheets

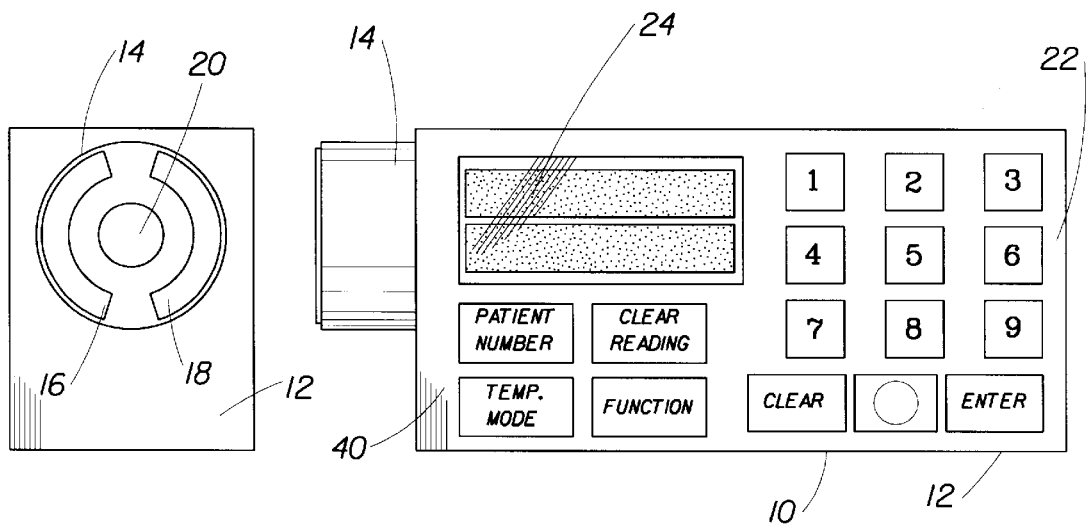
Fig. 5    Fig. 4
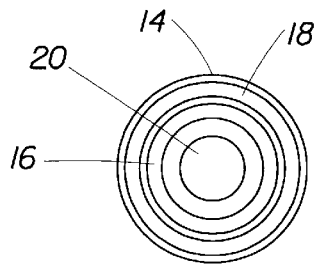    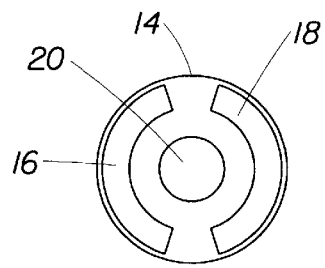
Fig. 6    Fig. 8
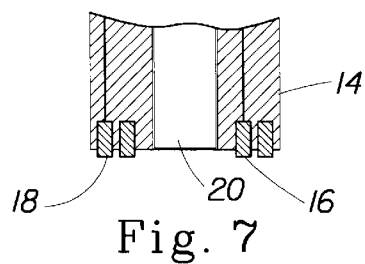    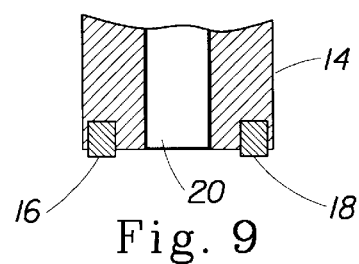
Fig. 7    Fig. 9

SELECTIVE TISSUE CONDUCTANCE/THERMOGRAPHY SENSOR APPARATUS

TECHNICAL FIELD

This invention relates to devices for measuring or displaying electrical and thermal characteristics of living tissue such as that of a human being or animal. Specifically, the present invention measures tissue conductivity and temperature in a localized region for the purpose of assessing pain, abnormal sensation, or sympathetic dysfunction in a human being or animal.

BACKGROUND OF THE INVENTION

Various methods and machines have been used in the past to measure electrical characteristics of living tissue for the purpose of locating an area of abnormal nervous system activity. U.S. Pat. No. 4,697,599, issued Oct. 6, 1987, to William Woodley and David Longmire describes such an apparatus and its use. This patent should be carefully considered for the purpose of putting the present invention into proper context.

A device known as the EPI-SCAN 5000, manufactured by the Epi-Scan Corporation of Russellville, Ala., represents an embodiment of the U.S. Pat. No. 4,697,599. One clinical use of this device is to objectively assess mediation, maintenance or clinical expression of certain pain forms through the sympathetic nervous system. Localized variance in skin conductance levels can be an indication of sympathetically-mediated or maintained pain. Detection of such abnormalities may be used to indicate certain pain therapies, such as insertion of a "nerve block."

SUMMARY OF THE INVENTION

The present invention provides a diagnostic device for assessing pain, abnormal sensation or sympathetic dysfunction in a human being or animal. This is accomplished by measuring tissue conductance and temperature in a selected region for localizing sympathetic nerve dysfunction. The device comprises two spaced-apart electrodes mounted together for measuring conductance of human or animal tissue over a selected region. A temperature sensor is positioned adjacent the electrodes for measuring tissue temperature in the selected region. A circuit is provided for indicating measured temperature and conductance to a user for localizing a region of sympathetic nerve dysfunction.

The conductance-sensing electrodes may be mounted either concentrically with the temperature sensor positioned substantially centrally thereof or each electrode may comprise an arcuate member positioned radially outwardly from the temperature sensor. In preferred form, the temperature sensor comprises an infrared thermocouple. A visual and/or audible signal may be used to indicate measured temperature and conductance. In preferred form, the device includes onboard memory for storing measured temperature and conductance data and may include an interface for downloading stored data to a separate computer.

Also in preferred form, the temperature sensor may be operated separately from the measurement of conductance. In this manner, the device may be used to thermally scan and locate a portion of tissue showing differential temperature prior to using the temperature and conductance sensors together to pinpoint a location of abnormal nerve activity.

Further uses, benefits and features of the present invention will be seen from a review of the detailed description of preferred embodiments, the various figures of the drawing and the appended claims, all of which constitute part of the disclosure of the present application.

BRIEF DESCRIPTION OF THE DRAWINGS

Like reference numerals are used to indicate like parts throughout the various figures of the drawing, wherein:

FIG. 4 is a front view of the device shown in FIG. 1;

FIG. 5 is an end view of the device shown in FIG. 1;

FIG. 6 is an end view of a concentric electrode/temperature sensor arrangement according to one embodiment of the present invention;

FIG. 7 is a sectional view taken along line 7—7 of FIG. 6;

FIG. 8 is a non-concentric arrangement of electrodes and temperature sensor according to a second embodiment of the present invention; and FIG. 9 is a sectional view taken substantially along line 9—9 of FIG. 8.

BEST MODE FOR CARRYING OUT THE INVENTION

Figure 1:
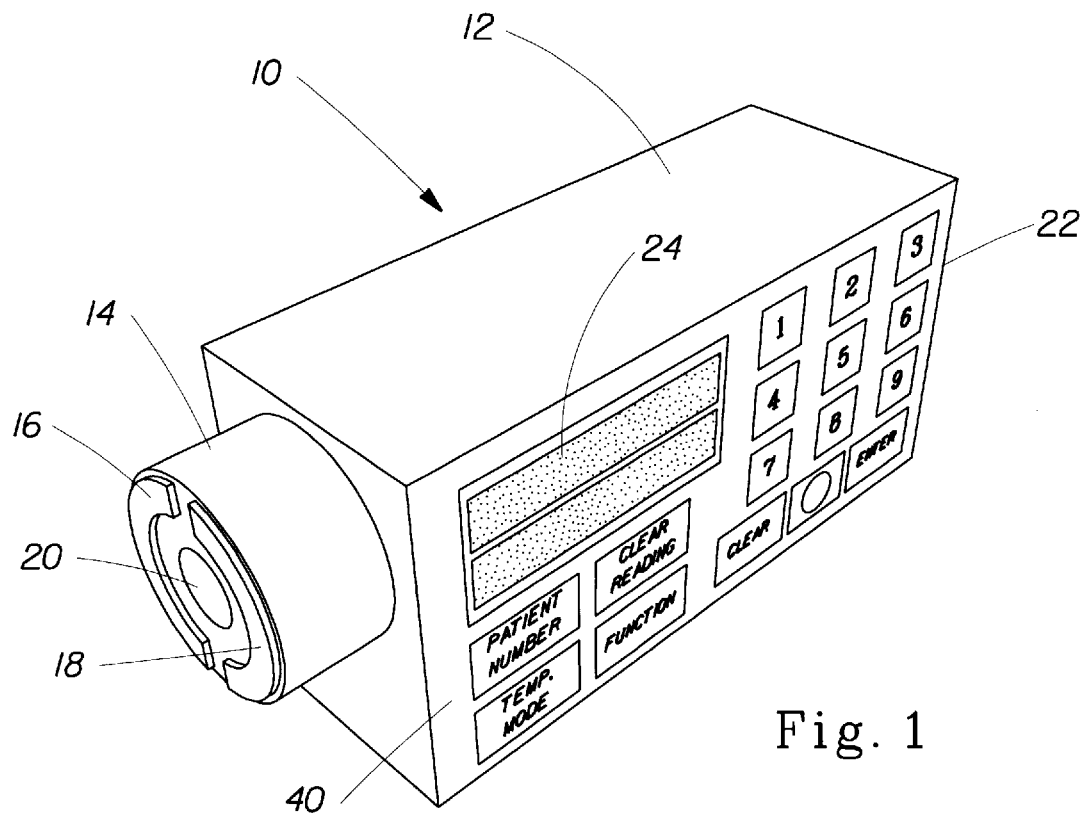
FIG. 1 is a pictorial view of a preferred embodiment of the selective tissue conductance/thermography sensor apparatus of the present invention.

Referring now to the various figures of the drawing, and first to FIG. 1, therein is shown at 10 a preferred embodiment of the diagnostic device of the present invention. The device includes a housing 12 sized to be held in the hand of the physician or other medical professional using the device. At one end is a sensor head 14 which includes a pair of electrode surfaces 16, 18 and a centrally-positioned infrared temperature sensor 20. In preferred form, the unit is powered by a battery that will fit within the housing 12. On one side of the housing 12 is a keyboard 22 and a display screen 24. The keyboard 22 may be used for programming the device or entering patient data into onboard memory. The display 24 provides the user with clinical data from which an assessment or diagnosis may be made.

Figure 2:
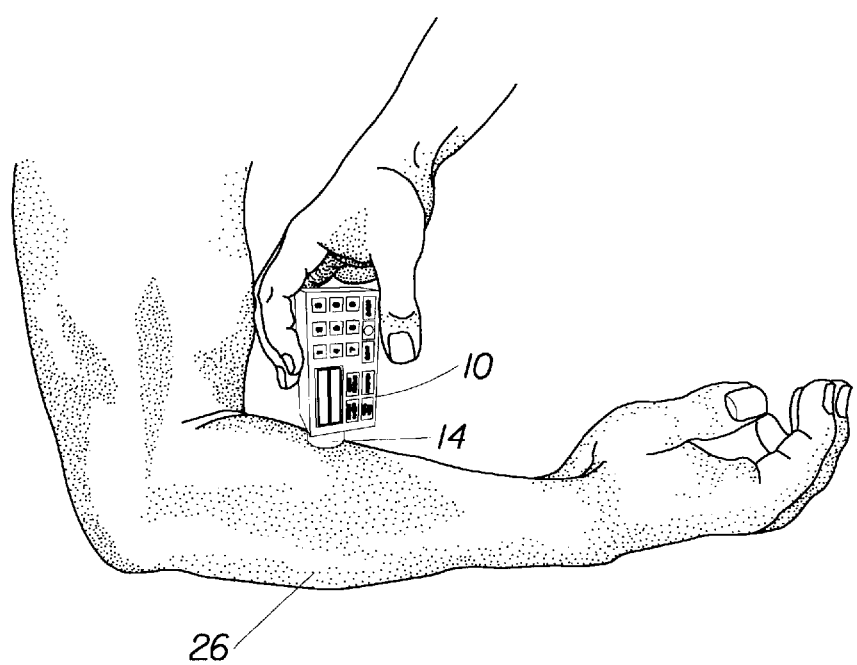
FIG. 2 is a schematic illustration showing how the device of FIG. 1 is used to obtain a tissue conductance/thermography reading.

FIG. 2 shows a general illustration of how the device 10 is used. The sensor head 14 is placed in contact with the patient's skin 26 and moved along the surface for sensing regional skin conductivity and temperature.

Referring to FIGS. 6 and 7, therein is shown a first preferred embodiment of a sensor head 14 in which the electrode surfaces 16, 18 are concentric with the infrared temperature sensor 20 centrally positioned. FIGS. 8 and 9 show a second preferred embodiment of the sensor head 14 in which the electrode surfaces 16, 18 have an arcuate shape and are positioned radially adjacent to the infrared temperature sensor 20.

A general discussion regarding the use of selected tissue conductance may be found in U.S. Pat. No. 4,697,599. The specification of this patent is incorporated herein by reference.

Figure 3A:
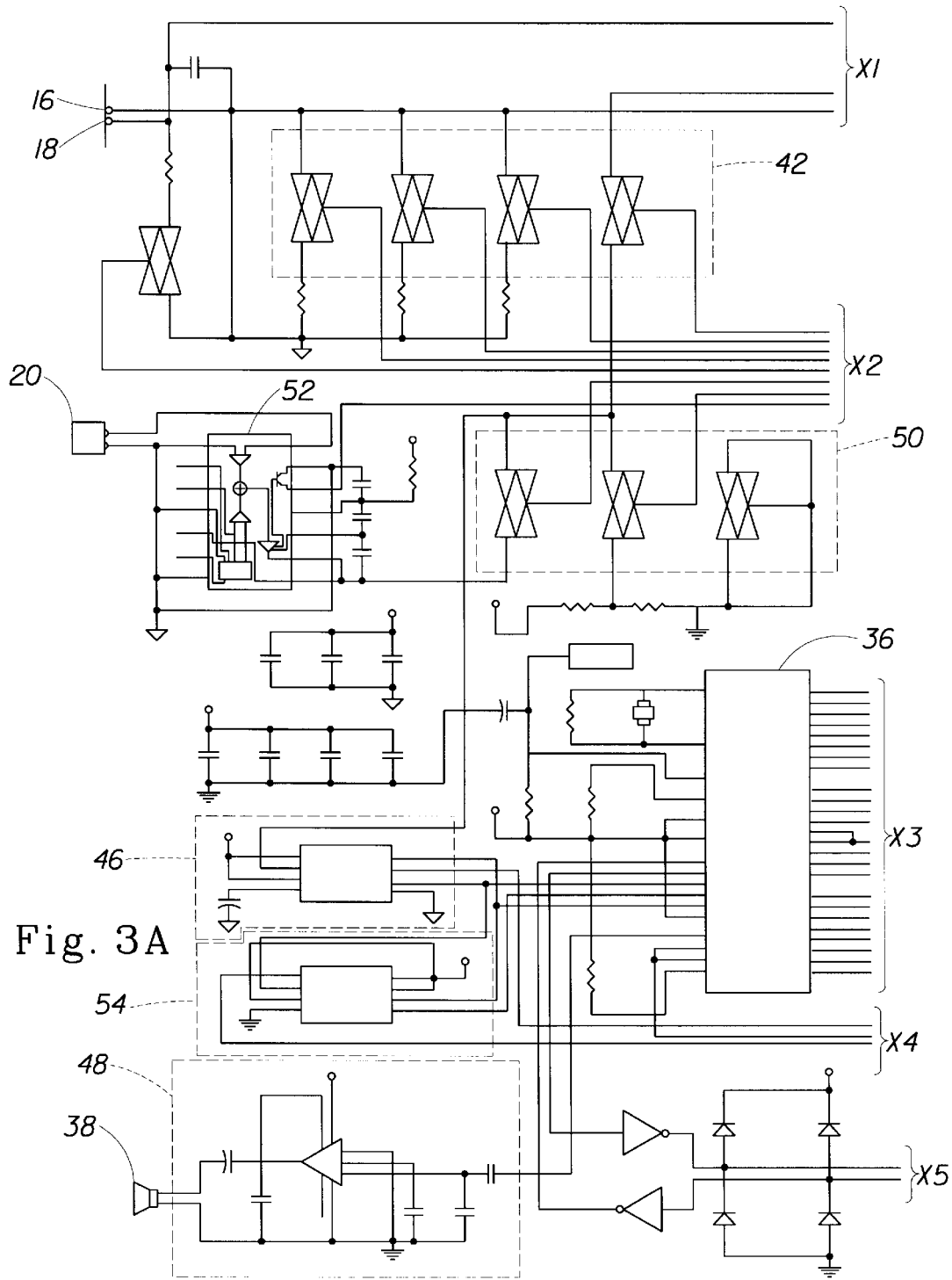
FIGS. 3A and 3B together represent a schematic circuit diagram of the preferred electrical circuit for the diagnostic device of the present invention.
Figure 3B:
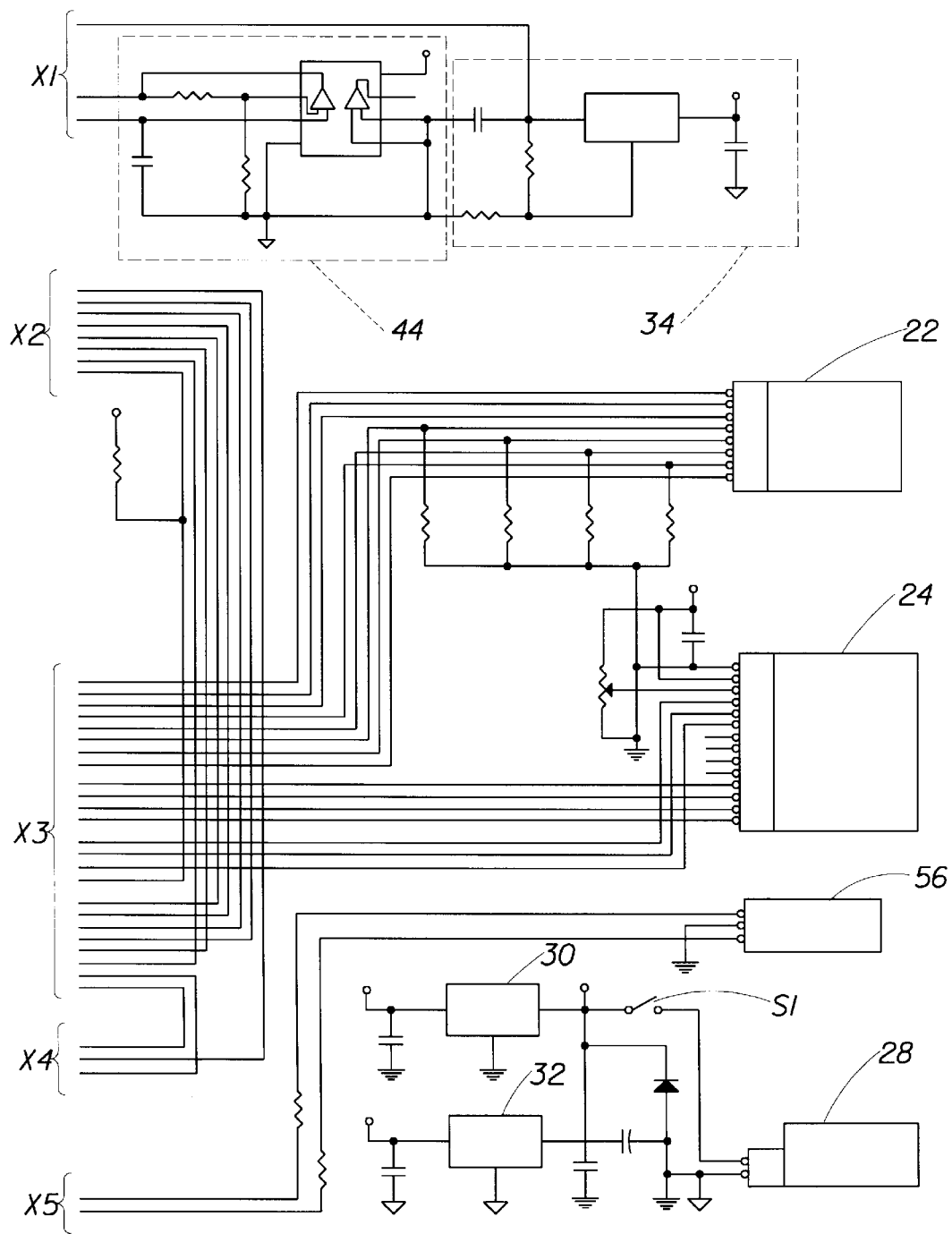

Referring now to FIGS. 3A and 3B, taken together, therein is shown a schematic circuit diagram of the preferred embodiment of the present invention. Power to the circuit is provided by a typical 9-volt battery 28. Voltage is applied to terminals 1 and 2 of JP1. A main power switch S1 is provided for connecting and disconnecting the power source 28.

The on/off switch S1 provides power to the unit from the battery 28 through three voltage regulators 30, 32, 34. The first voltage regulator 30 supplies power to the micro-controller unit 36, digital circuitry, and the LCD display 24. A second regulator 32 provides power to the analog circuitry and the third 34 provides a reference voltage ($V_{ref}$) for the selective tissue conductance measurements. This use of multiple voltage regulators isolates the digital power from the analog power and provides cleaner power to the analog circuitry for accurate measurements.

When the unit is powered on, "SELF TEST" is displayed on the LCD display 24 and the micro-controller unit 36 runs a self test subroutine and tests the battery condition, selective tissue conductance (STC)calibration, and infrared thermocouple 20. In preferred form, the LCD display 24 displays in two lines, eight characters per line, such as the Optrex™ DMC50448N. If all are found to be within operating parameters, the unit displays "SELF TEST OK" for about ¾ of a second and gives a two frequency "SELF TEST OK" beep from the speaker 38. A log-on message of up to eight ASCII characters by two lines may then be displayed until a measurement is taken or a function key 40 is pressed. The log-on message may be programmed by the factory or dealer and may contain the doctor's name or other identifying indicia.

If the selective tissue conductance calibration test or the thermocouple 20 fail the self check, the unit will display "STC CAL ERROR" or "TEMP ERROR" and beep five times at about 3.5 second intervals. If the battery 28 is too low for accurate measurements, the unit will display "REPLACE BATTERY" and beep five times at about 10 second intervals. In either case, this is a fatal error and the unit will not take any measurements and will continue to beep until powered down.

The present invention combines two sensory modes for virtually simultaneous operation. The first sensory mode is selective tissue conductance (STC). The second is a temperature measurement, or thermography, taken at a location immediately adjacent the measurement of selective tissue conductance. Together, these measurements provide the medical professional using the device with more reliable and precise information for assessing pain location, abnormal sensation or sympathetic nerve dysfunction.

The selective tissue conductance mode operates when the probes 16, 18 of the sensor head 14 are placed against the skin (or other conductive surface). A steady 1.41 volt current flows from $V_{ref}$ through the skin and through a 100K ohm resistor R8. By default, the scaling circuit 42 selects a x1 range. The voltage drop through the 100K ohm resistor R8 is sensed and amplified 11.0 times by the LMC662 operational amplifier (OP AMP) 44. The output of the OP AMP 44 is fed into the MAX187 analog-to-digital convertor IC46 and is read in binary as a raw voltage by the micro-controller unit 36. The micro-controller 36 senses the voltage, waits 200 milliseconds for the reading to stabilize, then takes another reading to be processed. If this reading is over 1085 nanoseimens per square centimeter ($nS/cm^2$), the reading is over range and the micro-controller 36 switches to a x10 range using a second 74HC4066 integrated circuit in the scaling circuit 42, now using a 10K ohm resistor R9 and reads the selective tissue conductance value again. Likewise, if this reading is over range, the micro-controller 36 switches the scaling circuit 42 to use a 1K ohm resistor R10, again reading the selective tissue conductance value in a x100 range. If over range again, the unit beeps three times and displays "OVERANGE" on line 1 of the LCD display 24. The voltage read is converted mathematically by the micro-controller into two binary addresses. The first address fetches a binary coded decimal selective tissue conductance value from a table in the micro-controller's memory and is converted into an ASCII value by the micro-controller 36. The selective tissue conductance value is then displayed on the top line of the LCD display 24 as a value calibrated in nanoseimens per square centimeter ($nS/cm^2$).

The second binary address fetches a binary number from another table in the micro-controller's memory corresponding to a frequency equal to ½ the selective tissue conductance value and loads this value into the output compare register in the micro-controller 36. The output compare interrupts are turned on and the desired frequency is output from pin number 38 of the micro-controller 36. This frequency, in the form of a tone, is amplified by an LM386 audio amplifier 48 and fed into the speaker 38. The unit will beep once before the tone is output if the X10 range has been auto-selected, or beep twice before the tone is output if the X100 range has been auto-selected. The LCD display 24 will fill with trailing zeros to make the higher ranges display be true selective tissue conductance value accurate to the three or four most significant digits. The tone continues until the sensor is removed from the conductance source (skin) and does not change frequency. This is known as a "true sample and hold." The value displayed on the LCD display 24 holds until the next reading is taken.

During the time that selective tissue conductance is being sensed, more than enough time will have elapsed to stabilize the thermocouple 20 for an accurate reading. In preferred form, an infrared thermocouple such as that manufactured by Exergen™, Part No. Irt/C.01J-98.6F/37C, is used. Using a 74HC4066 integrated circuit in the A/D source selector 50, the micro-controller 36 switches the input of the A/D convertor 46 from the selective tissue control op amp 44 to the output of a monolithic thermocouple amplifier 52. In preferred form, this amplifier 52 is an AD594 monolithic thermocouple amplifier with cold junction compensation integrated circuit. The output of this integrated circuit 52 now contains a voltage (calibrated to 10 millivolts per degree C., and read to 1 millivolt) equal to the temperature read by the thermocouple 20. This voltage is fed into the A/D convertor 46 and is read by the micro-controller 36. The temperature is read eight times and averaged by the micro-controller 36 for a more accurate reading. The micro-controller 36 converts this voltage to degrees and tenths of degrees C. and then converts this value to an ASCII number and output to line 2 of the LCD display 24.

The conductance and temperature values are added (or subtracted if a negative number) to the calibration values stored in the EEPROM 54 before the above-described conversion takes place and the values are displayed and stored. This allows the unit to be calibrated very precisely at the factory by automated test equipment without using mechanical devices such as trimpots, variable capacitors, etc., that can get out of calibration due to impact, vibration, or component aging.

A "store readings" mode may be turned on by entering a patient number from the keypad 22 and is indicated by a "C" (for "DATA Collection") on line 2 of the LCD display 24. In the "store readings" mode, the selective tissue conductance and temperature values are now stored by the micro-controller 36 into the EEPROM storage device 54 along with the previously-entered patient number for later download into a computer for record keeping and/or graphics charting. In preferred form, the EEPROM is a Xicor™ X25128. This EEPROM 54 will store over 16,000 bytes of information before a download is required. A bi-directional port 56 in the form of a modular jack provides an RS-232 serial interface for bi-directional data transfer to a separate computer (not shown) for downloading data, for automated test equipment calibrating, and testing of the unit. Alternatively, an IR interface or other similar means may be used.

The unit may be operated in a "temperature mode" by pressing the TEMP MODE key on the keypad 22, 40. This mode of operation is indicated by a "T" (for "temperature") in the first character position of line 2 on the LCD display 24. In this mode of operation, the temperature is read continuously and displayed on line 2 of the LCD display 24. A tone relative to the temperature, rather than selective tissue conductance, is output through the speaker 38. The tone is squelched for temperatures under 24° C. or over 43° C. to quiet the unit when out of the expected reading range. The selective tissue conductance reading is also displayed on line 1 of the LCD display 24 while in temperature mode. Alternatively, zeros are displayed if no valid reading is present.

The temperature mode may be used without the sensor head 14 being in direct contact with a patient's skin. In this manner, the unit may be used to quickly locate a general region of relative increased or decreased skin temperature prior to pinpointing a region of relative selective tissue conductance for assessing sympathetic nerve dysfunction.

Other features of this device include being able to test and, if necessary, indicate, the battery condition when powered on and every thirty seconds thereafter. When the battery has about thirty minutes of life remaining, the unit is programmed to give an audible signal from the speaker 38 (beep three times) and display "BATTERY LOW" on the LCD display 24 while remaining fully operational and accurate. The device will display a different audible signal (beep five times) and display "REPLACE BATTERY" before the low battery condition can cause any reading inaccuracies. Once "REPLACE BATTERY" is displayed, the unit will continue to provide the audible signal every ten seconds and will no longer take any measurements.

The "CLEAR READING" key clears the last reading taken from memory in case the user takes any reading in error. Pressing this key again will continue to clear each previous reading until all readings for that patient number have been cleared.

After five minutes of inactivity (i.e., no readings taken and no keys pressed), the unit 10 will provide an audible signal (beep twice) to remind the operator to turn off the power. The unit will continue to provide this signal every thirty seconds thereafter until turned off or used. Standard decoupling is used throughout (0.1 $\mu$F capacitors on each integrated circuit) and noise reduction capacitors used where necessary.

This invention provides many important improvements over the prior art. First, it combines temperature sensing using thermocouple technology in addition to selective tissue conductance readings. This hardware is very rugged and takes fast and accurate temperature readings. Ranging of selective tissue conductance is achieved automatically and the user need not interrupt testing to change ranges. Selective tissue conductance and temperature readings may be collected and displayed simultaneously. The "sample and hold" circuitry prevents the selective tissue conductance reading from wandering upward if the electrodes 16, 18 remain unmoved on the tissue surface. Data is automatically collected and stored for multiple patients and patient history. The collected data can be downloaded to a separate computer for record keeping and graphical charting of patient progress through the bidirectional port 56. This port 56 can also accept data or function changes from a separate computer allowing reprogramming, testing and calibration with ease.

The preferred embodiment described above may be subject to many modifications or reconfigurations without departing from the spirit and scope of the present invention. For this reason, our patent protection is not to be limited by or to the described preferred embodiment, but rather by the following claim or claims interpreted according to doctrines of claim interpretation, including the doctrine of equivalence and reversal of parts.

What is claimed is:

1. A diagnostic device for assessing pain, abnormal sensation or sympathetic dysfunction in a human being or animal, comprising:

two spaced-apart electrodes mounted together for measuring conductance of human or animal tissue over a selected region;

a temperature sensor positioned adjacent the electrodes for measuring tissue temperature in the selected region, said temperature sensor adapted to be used both with and without the temperature sensor being in direct contact with a subject's skin; and circuit means for indicating measured temperature and conductance to a user for localizing a region of sympathetic nerve dysfunction.

2. The device of claim 1, wherein the electrodes are mounted concentrically with the temperature sensor positioned substantially centrally thereof.

3. The device of claim 1, wherein each electrode comprises an arcuate member positioned radially outwardly from the temperature sensor.

4. The device of claim 1, wherein the temperature sensor comprises an infrared thermocouple.

5. The device of claim 1, wherein the means for indicating the measured temperature and conductance comprises a visual display.

6. The device of claim 1, wherein the means for indicating measured temperature and conductance comprises an audible signal.

7. The device of claim 6, wherein said audible signal comprises relatively higher pitched audible frequencies corresponding with one of relatively higher temperature measurements and relatively higher conductance measurements.

8. The device of claim 1, further comprising a memory means for storing measured temperature and conductance data.

9. The device of claim 8, further comprising an interface port for sharing stored data with a separate computer device.

10. The device of claim 1, wherein the temperature sensor may be operated separately from the measuring of conductance.

11. The device of claim 1, wherein said circuit means for indicating measured temperature and conductance to a user comprises a means for sampling and holding a conductance reading so long as said electrodes remain in contact with a subject's skin.

12. The device of claim 1, wherein said circuit means includes a scaling circuit adapted to select an appropriate range of conductance measurements based on a subject's conductance reading whereby a user may use said device without a need to interrupt conductance testing to change ranges.

* * * * *